(12) United States Patent
Nelis et al.

(10) Patent No.: US 9,163,341 B2
(45) Date of Patent: Oct. 20, 2015

(54) MULTIFILAMENT YARN CONSTRUCTION

(75) Inventors: Mischa Nelis, Geleen (NL); Roelof Marissen, Geleen (NL); Mandy Maria Jozefina Wiermans, Geleen (NL)

(73) Assignee: DSM IP ASSETS B.V., Heerlen (NL)

( * ) Notice: Subject to any disclaimer, the term of this patent is extended or adjusted under 35 U.S.C. 154(b) by 263 days.

(21) Appl. No.: 13/695,466

(22) PCT Filed: Apr. 29, 2011

(86) PCT No.: PCT/EP2011/056855
§ 371 (c)(1),
(2), (4) Date: Jan. 11, 2013

(87) PCT Pub. No.: WO2011/135082
PCT Pub. Date: Nov. 3, 2011

(65) Prior Publication Data
US 2013/0205979 A1    Aug. 15, 2013

(30) Foreign Application Priority Data

Apr. 29, 2010  (EP) .................................... 10161483

(51) Int. Cl.
| | | |
|---|---|---|
| *D04C 1/12* | (2006.01) | |
| *A61L 17/04* | (2006.01) | |
| *D02G 3/36* | (2006.01) | |
| *D02G 3/04* | (2006.01) | |
| *D02G 3/44* | (2006.01) | |

(52) U.S. Cl.
CPC . *D04C 1/12* (2013.01); *A61L 17/04* (2013.01); *D02G 3/045* (2013.01); *D02G 3/36* (2013.01); *D02G 3/448* (2013.01)

(58) Field of Classification Search
CPC ...... D07B 1/02; D07B 1/04; D07B 2201/102; D07B 2201/209; D07B 2201/1096; D07B 2201/2056; D07B 2201/2066; D07B 2201/2068; D04C 1/12; D02G 3/36; D02G 3/045; D02G 3/448; A61L 17/04
See application file for complete search history.

(56) References Cited

U.S. PATENT DOCUMENTS

| | | | | |
|---|---|---|---|---|
| 3,036,490 | A  * | 5/1962  | Muller et al. ......................... | 87/6 |
| 3,073,209 | A  * | 1/1963  | Benk et al. .......................... | 87/6 |
| 3,968,725 | A    | 7/1976  | Holzhauer | |
| 4,321,854 | A  * | 3/1982  | Foote et al. ......................... | 87/6 |
| 5,060,549 | A  * | 10/1991 | Beal .................................. | 87/6 |
| 5,301,595 | A  * | 4/1994  | Kessie ............................... | 87/6 |
| 7,047,860 | B2 * | 5/2006  | Faborsky ............................ | 87/6 |

(Continued)

FOREIGN PATENT DOCUMENTS

| | | |
|---|---|---|
| EP | 1 293 218 | 3/2003 |
| WO | WO 89/01320 | 2/1989 |

OTHER PUBLICATIONS

International Search Report for PCT/EP2011/056855, mailed Aug. 23, 2011.

(Continued)

*Primary Examiner* — Shaun R Hurley
(74) *Attorney, Agent, or Firm* — Nixon & Vanderhye P.C.

(57) ABSTRACT

The invention concerns a multifilament yarn construction comprising a core part and a sheath part, the core part comprising a plurality of core filaments, and the sheath part comprising a plurality of sheath filaments. Furthermore, the invention concerns members comprising the multifilament yarn construction and uses of the multifilament yarn construction and the members according to the invention.

24 Claims, 5 Drawing Sheets

(56) References Cited

U.S. PATENT DOCUMENTS

| 7,703,372 B1 * | 4/2010 | Shakespeare | 87/6 |
| 8,136,438 B2 * | 3/2012 | Shakespeare | 87/6 |
| 2008/0009903 A1 * | 1/2008 | Schmieding et al. | 606/228 |

OTHER PUBLICATIONS

Written Opinion for PCT/EP2011/056855, mailed Aug. 23, 2011.
JPO Official Action, Patent Application No. P2013-506679 (Apr. 2, 2015).

* cited by examiner

MULTIFILAMENT YARN CONSTRUCTION

This application is the U.S. national phase of International Application No. PCT/EP2011/056855 filed 29 Apr. 2011 which designated the U.S. and claims priority to EP 10161483.2 filed 29 Apr. 2010, the entire contents of each of which are hereby incorporated by reference.

TECHNICAL FIELD OF THE INVENTION

The invention relates to a multifilament yarn construction, such as a rope, a cable or a suture, the construction comprising a plurality of multifilament yarns. More particularly, the invention relates to a multifilament yarn construction having yarns arranged in a core part and a braided sheath part. Furthermore, the invention relates to uses of such multifilament yarn constructions.

BACKGROUND OF THE INVENTION

Multifilament yarn core/sheath constructions are known. An example of such a construction is US 200810009903A1. Multifilament yarn core/sheath constructions are typically utilized to obtain a construction with lower bending fatigue. Furthermore, multifilament core/sheath constructions typically behave plastic upon bending without much—if any—elastic deformation. The plasticity under bending is typically associated with local bending stresses. In other words, the resistance against bending deformation is very small.

When the yarn is a thermoplastic yarn, the stiffness of multifilament yarn constructions may be increased by heat treating the construction to a level where the yarns at least partially fuse together to form a monofilament-like sheath for example as disclosed in EP 1 771 213. However, monofilaments and monofilament-like constructions typically behaves elastic upon bending at smaller bending angles without leaving much—if any—plastic deformation after removal of the bending force. For large bending at sharp angles monofilament and monofilament-like constructions may deform plastically, however, such plastic deformation will introduce considerably damage to the monofilament construction.

Other multifilament core/sheet construction are disclosed in U.S. Pat. No. 3,968,725 (Holzhauer), EP 1 293 218 (Grafton et al.) and WO 2009/142766.

OBJECTS OF THE INVENTION

It is the object of the invention to provide a multifilament yarn construction, where the construction exhibit improved properties.

It is another object of the invention to provide uses of the improved multifilament yarn construction.

The improvement may for example be increased stiffness, compactness and/or handleability of a construction according to the first aspect of the invention and yarn constructions comprising the segment.

DISCLOSURE OF THE INVENTION

The object of the invention is achieved by a multifilament yarn construction which construction comprises a core part and a sheath part.

The core part comprises a plurality of core filaments. The core filaments may be arranged in one or more multifilament yarns or be a collection of monofilaments. The core filaments may advantageously be arranged in parallel or substantially in parallel, which allows for the most efficient utilization of the strength of the core filaments. If the core consists of one multifilament yarn, it is preferred that the yarn is twisted with a twist level of less than 100 turns per meter. If the core consist of more than one multifilament yarns, such as at least 3 multifilament yarns, or more than one monofilaments it is preferred that the multifilament yarns or the monofilaments are arranged in a braided, plaited, plied or twisted construction. Most preferred is a braided core construction, such as a one over one (see FIG. 2) of for example four, six, eight, twelve or sixteen yarns or monofilaments. It was found to be advantageous to utilize a braid of eight or sixteen multifilament yarns in the core as this provided a very stable construction. In another embodiment, it was preferred to have a core of one or more multifilament yarns arranged substantially parallel to the length of the construction.

The sheath part comprises a plurality of sheath filaments. The sheath part is braided onto the core part. The sheath filaments may be arranged in multifilament yarns or the sheath filaments may be monofilaments so that the sheath is braided from multifilament yarns and/or monofilament yarns. It is preferred that the sheath filaments are comprised in multifilament yarns as it was found to allow for easy manufacturing by readily available and affordable starting material. The braid may for example be a one over one (see FIG. 2), two over one (see FIG. 3) or three over one (not shown) of for example four, six, eight, twelve or sixteen yarns or monofilaments. It was found to be highly advantageous to utilize a braid of eight or sixteen multifilament yarns in a one over one diamond braid as this allowed for a high stitch level and the best binding between the yarns of the sheath with high braiding angle and high fill factor and was found to lead to the stiffest multifilament yarn constructions according to the invention.

The sheath part of the multifilament yarn construction according to the first aspect of the invention is between 4 to 75 area-% of a cross section of the multifilament yarn construction. By area of cross section is herein meant the area in a plane orthogonal to the length of the multifilament yarn construction. Furthermore, the braiding angle of the sheath part is at least 30°. The braiding angle is the angle between the sheath filaments and a plane parallel to the length of the multifilament yarn construction according to the invention. The braiding angle is calculated as described below. A sketch in U.S. Pat. No. 3,968,725 (Holzhauer) discloses a construction with a pitch of 30 per foot (see data on sheet in experimental part). This corresponds to a braiding angle of about 30° for a diameter of 0.3 inch (=7.6 mm), which is hence functionally far from the claimed braiding angles of the present invention, which also explains why no surprising stiffness was disclosed by Holzhauer.

Another further embodiment of the invention concerns a multifilament yarn construction comprising a core part and a sheath part. The sheath part comprises a plurality of core filaments, and the sheath part comprising a plurality of sheath filaments. The sheath part is between 4 to 40 area-% of a cross section of the multifilament yarn construction, and the sheath part is braided onto the core part. Furthermore, the ratio of the cross section area of the multifilament yarn construction to the theoretical cross section area of the multifilament yarn construction is at most 1.5, and the width of the multifilament yarn construction is between 0.2 to 5 mm. This aspect of the invention provides a very compact multifilament yarn construction.

Another further embodiment of the invention concerns a multifilament yarn construction comprising a core part and a sheath part. The sheath part comprises a plurality of core filaments, and the sheath part comprising a plurality of sheath filaments. The sheath part is between 4 to 75 area-% of a cross section of the multifilament yarn construction, and the sheath part is braided onto the core part. Furthermore, the flexural yield stress, $\sigma_{5\%}$, of the multifilament yarn construction according to the second aspect of the invention is at least 3 N/mm². The flexural yield stress, $\sigma_{5\%}$, is the apparent stress according to the assumption of elastic beam theory as assumed in ASTM D 790-07 (see below) in the multifilament yarn construction at 5% strain. The width of the multifilament yarn construction according to this aspect of the invention is between 0.2 to 5 mm. This embodiment of the invention optionally has a braiding angle of the sheath part of at least 30°.

Traditional multifilament yarn constructions are flexible as the multiple filaments are allowed to shift relative to each other when bend. Therefore it is highly surprising that the multifilament yarn construction according to the invention are stiff and behaves substantially as a solid bar when it comes to bending behaviour. This is observed as a tendency to be stiff and—if bend—stay stiff in the new shape. This is a highly advantageous property as it allows for example for turning the multifilament yarn construction around an obstruction without the need to lead the construction by the tip. An example of this is in a medical procedure, where the multifilament yarn construction is used in a medical suture and the suture needs to be moved around a bone without space for a guiding the suture. Another example is when a yarn construction needs to follow a guide pipe of significantly larger diameter than the multifilament yarn construction, where the multifilament yarn construction of the present invention reduces the risking of the yarn bugling inside the guide pipe.

BRIEF DESCRIPTION OF THE DRAWINGS

The invention will be explained more fully below with reference to exemplary embodiments as well as the drawings, in which.

All figures are highly schematic and not necessarily to scale, and they show only parts which are necessary in order to elucidate the invention, other parts being omitted or merely suggested.

DETAILED DESCRIPTION

Figure 1:
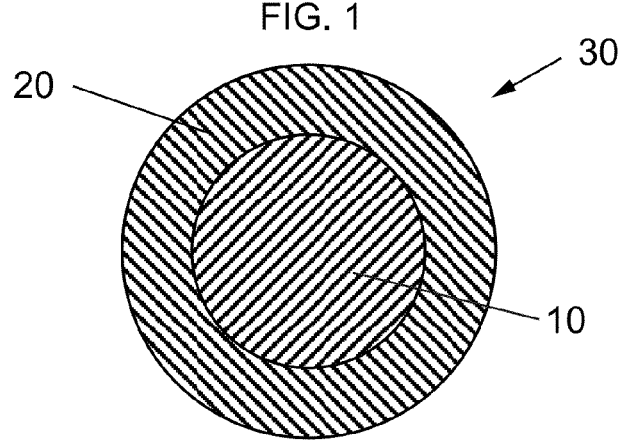
FIG. 1 shows a schematic representation of a cross section of a core sheath multifilament yarn construction.
Figure 2:
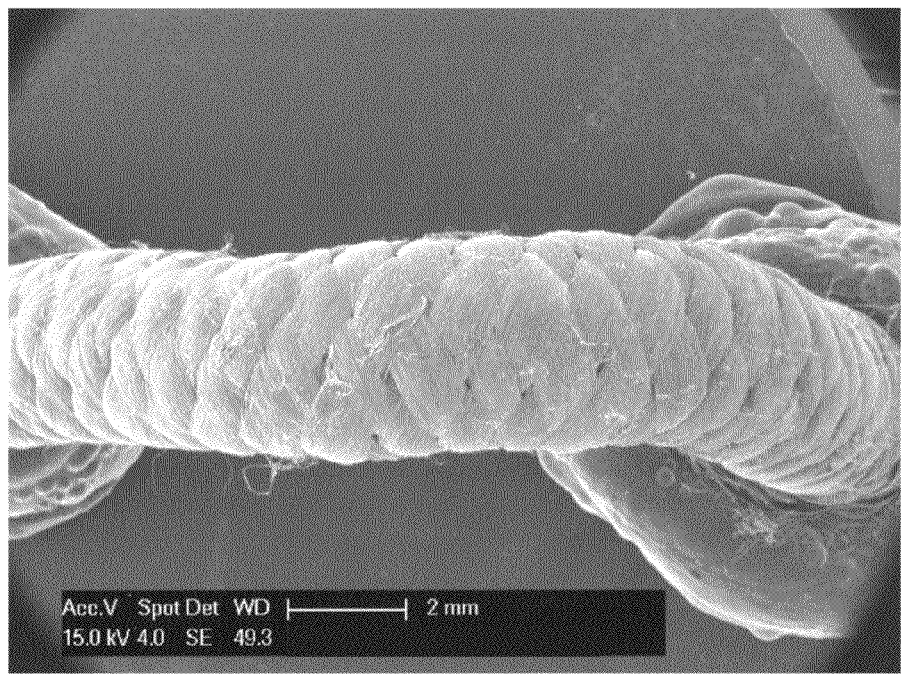
FIG. 2 shows a bended multifilament yarn construction with a one over one sheath braiding.
Figure 3:
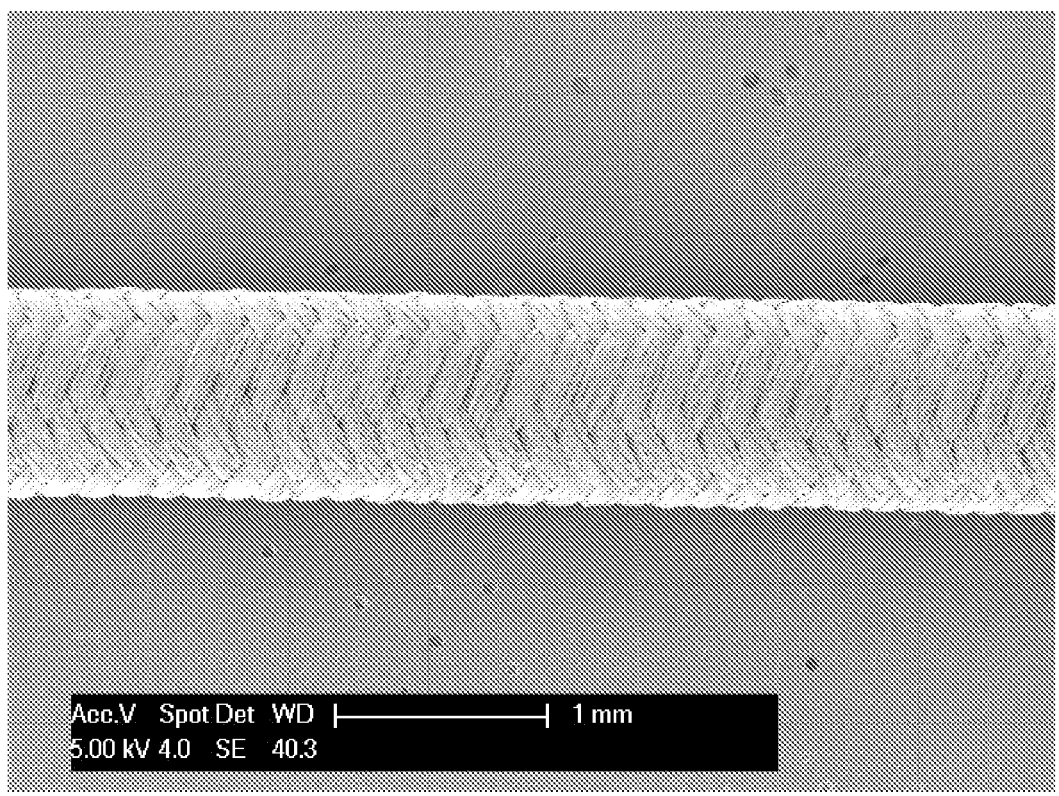
FIG. 3 shows a multifilament yarn construction with a two over two sheath braiding.

In FIG. 1 an example of a schematic cross section 30 of a core sheath multifilament yarn construction is shown. The core part 10 comprises a plurality of core filaments (not shown), and the sheath part 20 comprises a plurality of sheath filaments (not shown). In one embodiment, the core part or the sheath part may be coating for example to increase the stiffness of the construction, to introduce electrical isolation between the core and the sheath or between the multifilament yarn construction and the surrounding environment, or to introduce an active component, such as an antimicrobial agent or a growth factor. The coating may be of a covering, which substantially does not penetrate into the space between the filaments and/or the coating may be an impregnating coating, which may for example improve stiffness of the multifilament yarn construction.

By cross section is herein meant a section orthogonal to the length direction of the yarn construction.

By yarn construction is herein meant a combination of yarns arranged in a rope like construction (such as a rope, a cable, a suture, a string, a fishing line, etc.), a woven or non-woven textile construction, a net or a web.

In a highly preferred embodiment, the fill factor of the sheath part is at least 7. The fill factor is an indicator of the closeness of the arrangement of filaments (typically in multifilament yarns) on the surface of the core part. Below is a specification on calculation and determination of the fill factor in the present case. It was found that a high fill factor tended to increase the stiffness of the multifilament yarn construction. Higher fill factors such as a fill factor of at least 8 or 9 further enhanced the stiffness of the multifilament yarn construction and particularly advantageous was found to be a fill factor of at least 10. In general, if was found that the higher the fill factor, the stiffer the multifilament yarn construction. The maximum fill factor is dictated by structural limitation and depends on a number of parameters such as braiding angle and area ratio between core part and sheath part and may be determined experimental for the individual multifilament yarn construction configuration. However, as a rule of thumb, the fill factor is typically (but not necessarily) below 20.

In most cases, the cross section of the multifilament yarn constructions according to the invention is substantially circular. This is particularly the case for the multifilament yarn constructions according to the aspect of the invention relating to the high compactness embodiment. The cross section area of the multifilament yarn construction is calculated from the average diameter measured with a Laser ODAC 15XY by a dual-axis measuring. The theoretical cross section area is the area corresponding to the measured titer of the multifilament yarn construction assuming no porosity in the construction. Perfect compaction of the multifilament yarn into the construction corresponds to a ratio a/A=1, which would basically mean that the yarn is fully compacted and no air is entrapped inside the construction. According to this aspect of the invention, the ratio, a/A, of the cross section area of the multifilament yarn construction, a, to the theoretical cross section area of the multifilament yarn construction, A, should be at the most 1.5, however it was found to be highly advantageous that a/A is at most 1.3, and more preferably the ratio is at most 1.2, and yet more preferably at most 1.1. This may be reached by a combination of one or more of braiding angle (preferred are high braiding angles as discussed elsewhere), fill factor (preferred are high fill factors as discussed elsewhere), choice of yarn (preferred are high modulus fibres (with high longitudinal modulus) with relatively soft transverse modulus, such as gelspun HPPE yarn). The highly compact multifilament yarn constructions are highly advantageous for applications where low profile (diameter) of the yarn construction is important, such as for medical applications involving minimum invasive techniques.

A highly surprising feature of the multifilament yarn constructions of the present invention was that upon repeatedly bending the decrease in flexural yield stress was limited and the strength of the multifilament yarn construction was substantially unchanged. This combination of features (high strength and stiffness also after repeatedly bending) has been requested for the medical applications for long time. Therefore, a highly preferred embodiment of the multifilament yarn construction according to the invention has an exhausted flexural yield stress, $\sigma_{5\%,5}$, of more than 45% of flexural yield stress, $\sigma_{5\%}$, of the multifilament yarn construction. Particularly preferred are multifilament yarn construction where the exhausted flexural yield stress, $\sigma_{5\%,5}$, is at least 55% of flexural yield stress, $\sigma_{5\%}$, of the multifilament yarn construction.

The filaments of the core and the sheath may selected from a wide range of natural and synthetic fibers, however, it is preferred that at least 50 weight-% of the plurality of core filaments of the multifilament yarn construction and/or at least 50 weight-% of the sheath filaments of the multifilament yarn construction are selected from the group consisting of synthetic fibers such as polypropylene, nylon, polyesters, polyethylene, aramids and polyaramids. More preferably, at least the at least 90 weight-% of the plurality of core filaments of the multifilament yarn construction and/or at least 90 weight-% of the sheath filaments of the multifilament yarn construction are selected from the group consisting of synthetic fibers such as polypropylene, nylon, polyesters, polyethylene, aramids and polyaramids. Highest stiffness was found when the filaments were selected from high modulus filaments, such as filaments with an e-modulus of at least 5 GPa and even better with an e-modulus of at least 9 GPa. In a preferred embodiment at least 90 weight-% of the plurality of core filaments of the a multifilament yarn construction and/or at least 90 weight-% of the sheath filaments of the multifilament yarn construction are hence selected from the group consisting of high performance polyethylene (HPPE) and high performance aramids.

By HPPE is herein understood High Performance Polyethylene, which is yarn based on stretched polyethylene with a Young's modulus of at least 30 GPa. HPPE may for example be prepared by a meltspinning process (as for example disclosed in EP1445356), by solid state process (as for example disclosed in EP1627719) or by gelspinning (as for example disclosed in WO 2005/066401). A particularly preferred type of HPPE is gelspun ultra high molecular weight polyethylene (UHMWPE), where the UHMWPE has an intrinsic viscosity (IV) as measured on solution in decalin at 135° C., of at least 5 dl/g, preferably at least 10 dl/g, more preferably at least 15 dl/g, most preferably at least 21 dl/g. Preferably, the IV is at most 40 dl/g, more preferably at most 30 dl/g, even more preferably at most 25 dl/g. Gelspun UHMWPE typically has a Young's modulus of at least 50 GPa.

Particularly advantageous was HPPE, which is stretched polyethylene. The most preferred HPPE was gel spun UHMWPE, which combines extremely high tenacity, modulus and abrasion resistance. Hence, in a preferred embodiment of the invention at least 90 weight-% of the plurality of core filaments of the multifilament yarn construction and/or at least 90 weight-% of the sheath filaments of the multifilament yarn construction are gel spun UHMWPE.

In one embodiment, the core part and/or the sheath part comprises an electrically or optically conducting component, so that the multifilament yarn construction may conduct electricity (such as electrical signals or electrical power) or light (such as optical signals or power, like for example as a laser beam). In this embodiment, it is highly preferred that at least one of the core filaments or sheath filaments is high performance polyethylene (HPPE), as HPPE combines high strength and abrasion resistance and thereby reduces the risk that the electrically or optically conducting component will be damaged during use.

The ratio between area of the core part and the sheath part may vary considerably. In general, it was also observed that the higher the fraction of the area of the cross section that is accounted for in the sheath part, the higher the stiffness of the multifilament yarn construction when the filaments of the core part and the sheath part consist of the same material. Hence, in a preferred embodiment, the core part 10 is at least 25 area-% of the cross section 30 of the multifilament yarn construction 4a, more preferably the core part is at least 30 area-% of the cross section 30 of the multifilament yarn construction 4a, and when the strength of the multifilament yarn construction is particularly important, it is preferred that the core part is at least 35 area-% of the cross section 30 of the multifilament yarn construction. In a preferred embodiment of the multifilament yarn construction having a particularly high strength, the core part covers a large part of the cross section such as the core part being at most 96 area-% of the cross section 30 of the multifilament yarn construction 4a. For high stiffness multifilament yarn constructions, it was found to be advantageous that the core part accounted for at most 50 area-% of the cross section 30 of the multifilament yarn construction 4a, and more preferably the core part accounted for at most 40 area-% of the cross section 30 of the multifilament yarn construction 4a. For very high stiffness multifilament yarn constructions, the core part accounted for at most 35 area-% of the cross section 30 of the multifilament yarn construction 4a, such as for example at most 30 area-% of the cross section 30 of the multifilament yarn construction 4a.

It was also observed that the higher the fraction of the area of the cross section that is accounted for in the core part, the higher the strength when the filaments of the core part and the sheath part consist of the same material. In another embodiment, the multifilament yarn construction 4a according to the invention the core part was at least 80 area-% of the cross section 30 of the multifilament yarn construction 4a, and more preferably at least 85 area-% of the cross section 30 of the multifilament yarn construction 4a. For the highest strength multifilament yarn construction according to the invention, it was found to be advantageous that the core accounted for at least 90 area-% of the cross section 30 of the multifilament yarn construction 4a, such as at least 93 area-% of the cross section 30 of the multifilament yarn construction 4a. To ensure some stiffness for the highest strength multifilament yarn construction according to the invention, it was found that the core part preferably should account for at most 96 area-% of the cross section 30 of the multifilament yarn construction 4a, and more preferably at most 94 area-% of the cross section 30 of the multifilament yarn construction 4a.

The diameter of the multifilament yarn construction according to the invention may vary dependent on the application of the construction. For most applications, a width of between 0.2 mm to 5 mm is suitable. By width is herein meant the largest dimension of a cross section of the multifilament yarn construction orthogonal to the length direction of the multifilament yarn construction. It appears that for higher widths, the effect of the construction on the flexural yield strength is reduced, and the mere diameter of the construction seems to have an increased influence on the bending behaviour of the multifilament yarn construction. This also explains why no surprising stiffness was observed in U.S. Pat. No. 3,968,725 (Holzhauer) for a construction with a diameter of 0.3 inch (=7.6 mm).

For applications within sport, such as thin ropes for yachting and fishing lines, and medical applications, such as sutures, cables and actuators, width of 0.3 mm to 4 mm is suitable and most preferably widths of 0.4 mm to 3 mm provides the highest effect for applications as medical cables and sutures.

The tensile strength of the multifilament yarn construction according to the invention may considerably depend on the tensile strength of the filaments utilized for core and the sheath filaments. It is preferred—but not required to achieve some flexural yield strength—that the tensile strength of the multifilament yarn construction is at least 10 cN/dtex and more preferred at least 15 cN/dtex. This is for example achievable for multifilament yarn construction comprising HPPE optionally in combination with other types of filament, such as polyester or aramides. Most preferred are multifilament yarn construction with tensile strength of at least 20 cN/dtex, as these multifilament yarn construction allows for very high strength at very low construction width, which is highly requested for example in medical applications where minimum invasive techniques continues to push the limit of required material performance.

Highly surprisingly it was found that for the multifilament yarn construction according to the invention, the stiffness of the construction increases when the braiding angle was increased. This is contrary to the typical situation for fibrous materials, where alignment of fibers in the length direction tends to increase stiffness and alignment of fibers away from the length direction tends to decrease the stiffness. Therefore, for a preferred embodiment of the invention the braiding angle of the sheath part of the multifilament yarn construction 4a is at least 33° and more preferably the braiding angle of the sheath part is at least 35°. In a further embodiment, the braiding angle of the sheath part of the multifilament yarn construction 4a is at least 40°, and preferably the braiding angle of the sheath part of the multifilament yarn construction (4a) is at least 45° or even better at least 55°. Further, it was found that the most stiff multifilament yarn constructions was had a braiding angle of the sheath part of the multifilament yarn construction 4a of at least 60°.

It was also found that for extremely high braiding angles, the construction tended to be cumbersome and time consuming to prepare. In another embodiment the multifilament yarn construction 4a according to the invention therefore has a braiding angle of the sheath part is at most 75°, and preferably the braiding angle is at most 70°. Most preferably the braiding angle of the sheath part is at most 66°.

The multifilament yarn constructions 4a according to the invention are all stiff, but the stiffness varying dependent on the actual construction as well as the choice of filament material of the core part and—particularly—the sheath part. In one embodiment of the invention, the flexural yield stress, $\sigma_{5\%}$, of the multifilament yarn construction 4a is at least 3 N/mm$^2$, and preferably the flexural yield stress, $\sigma_{5\%}$, of the multifilament yarn construction 4a is at least 5 N/mm$^2$. For the more preferred embodiments the flexural yield stress, $\sigma_{5\%}$, of the multifilament yarn construction 4a is at least 7 N/mm$^2$, and more preferably the flexural yield stress, $\sigma_{5\%}$, of the multifilament yarn construction 4a is at least 15 N/mm$^2$. The best combination of construction parameters yields exhibited a flexural yield stress, $\sigma_{5\%}$, of the multifilament yarn construction 4a is at least 20 N/mm$^2$.

As too high stiffness is disadvantageous in some applications in one embodiment the flexural yield stress, $\sigma_{5\%}$, of the multifilament yarn construction 4a may optionally be less than 50 N/mm$^2$, such as less than 30 N/mm$^2$.

Another aspect of the invention concerns a member 2 comprising a multifilament yarn construction 4a according to the first aspect of the invention. In one embodiment, the member 2 is a sport appliance, such as a fishing line, yachting ropes or a kite line. Such members may tend to get entangled during use, and surprisingly it was found that if the member comprises the multifilament yarn construction according to the invention, the tendency to get entangled is reduced and the ability to disentangle the member is increased. The same is observed for ropes and rope constructions as well as nets like fishing nets and cargo nets. In another embodiment, the member is an antiballistic article.

In a particularly preferred embodiment of the invention, the member is a medical implant or a medical repair product, such as a suture, a cable or a mesh, where the combination of stiffness and ability to retain stiffness and strength after repeatedly bending is highly requested. For members to be used in medical applications it is particularly advantageous to utilize multifilament yarn constructions comprising HPPE filaments, as this further allows for very high strength and hence allow for further miniaturization required minimum invasive techniques. Another aspect of the invention hence concerns the use of a multifilament yarn construction 4a according to the first aspect of the invention or a member 2 according to the second aspect of the invention in a medical repair product. Particularly such use is advantageous when the medical repair product is a suture, a cable, or a mesh.

Due to the ability of the multifilament yarn construction to reduce entanglement and enhance disentanglement of member comprising the multifilament yarn construction, another aspect of the invention concerns the use of a segment 4a according to the first aspect of the invention or a member according to the second aspect of the invention for reducing knot formation or reducing knot strength. It is highly surprising that the construction has these highly useful abilities. It could be theorized without being limited thereto that these abilities are related to the stiffness of the multifilament yarn constructions compared to other yarn constructions of similar size.

Figure 8:
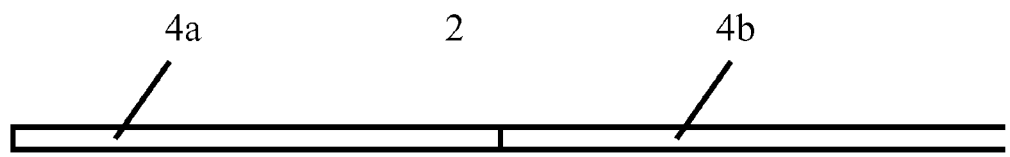
FIG. 8 shows a member comprising a multifilament yarn construction according to the invention.
Figure 9:
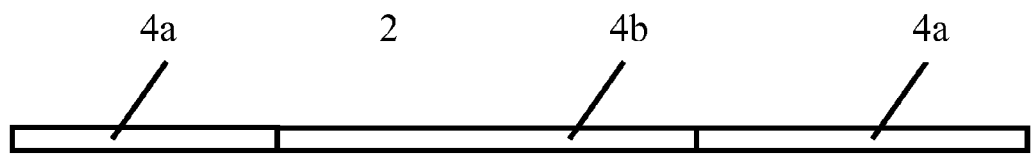
FIG. 9 shows another member comprising a multifilament yarn construction according to the invention.

A particularly type of members 2 according to the invention comprises both a multifilament yarn construction 4a according to the invention and a further multifilament yarn construction 4b, where the further multifilament yarn construction 4b is different from the multifilament yarn construction 4a according to the invention. This is illustrated in FIG. 8. Particularly, it was found to be advantageous when the further multifilament yarn construction 4b is NOT a multifilament yarn construction according to the invention. Particularly this allows for arranging of the stiff multifilament yarn constructions according to the invention in connection with a more flexible construction, so that the stiff part may be used for positioning the member and the flexible part may be used for knotting of the multifilament yarn construction once in place. Hence, it is particularly advantageous when the multifilament yarn construction 4a according to the invention is arranged near an end of the member (2) and even more preferably when the multifilament yarn construction 4a according to the invention is arranged near both ends of the member 2 with at least one further multifilament yarn construction 4b arranged between the multifilament yarn constructions 4a. This is illustrated in FIG. 9. It should be observed that FIG. 8 and FIG. 9 are not drawn to scale and that the length of the sections may vary considerably so that section 4a may be very short compared to section 4b or vice versa.

Braiding Angle Determination

The braiding angle, θ, is the angle between the braiding yarn at the surface of the yarn construction and the longitudinal axes of yarn construction. The braiding angle is defined in DIN 47250 as $$\theta = \arctan\left(\frac{\Pi D_m}{L}\right)$$

Here, θ is the braiding angle; $D_m$ is the average diameter of the construction and L is the stroke length. The diameter was measured with a Laser ODAC 15XY by a dual-axis measuring. The stroke length, L, was calculated from the stitch number, S, per cm and the number of strands, N. The stroke length is then $$L = \frac{10 \text{ mm}}{S} \frac{N}{2}$$

Fill Factor Determination

The fill factor, F, is a measure of the tightness of sheath yarns at the surface defined as $$F = \frac{\sqrt{t/\rho}}{d}$$

Here, t is the titer of the sheath yarns in tex (gram/km), d is the average distance between two parallel yarns in the cover in mm and ρ is the density in gram/cm³ of the sheath yarn polymer. For the utilized HPPE yarns ρ=0.975 and the utilized polyester yarns ρ=1.37.

Figure 4:
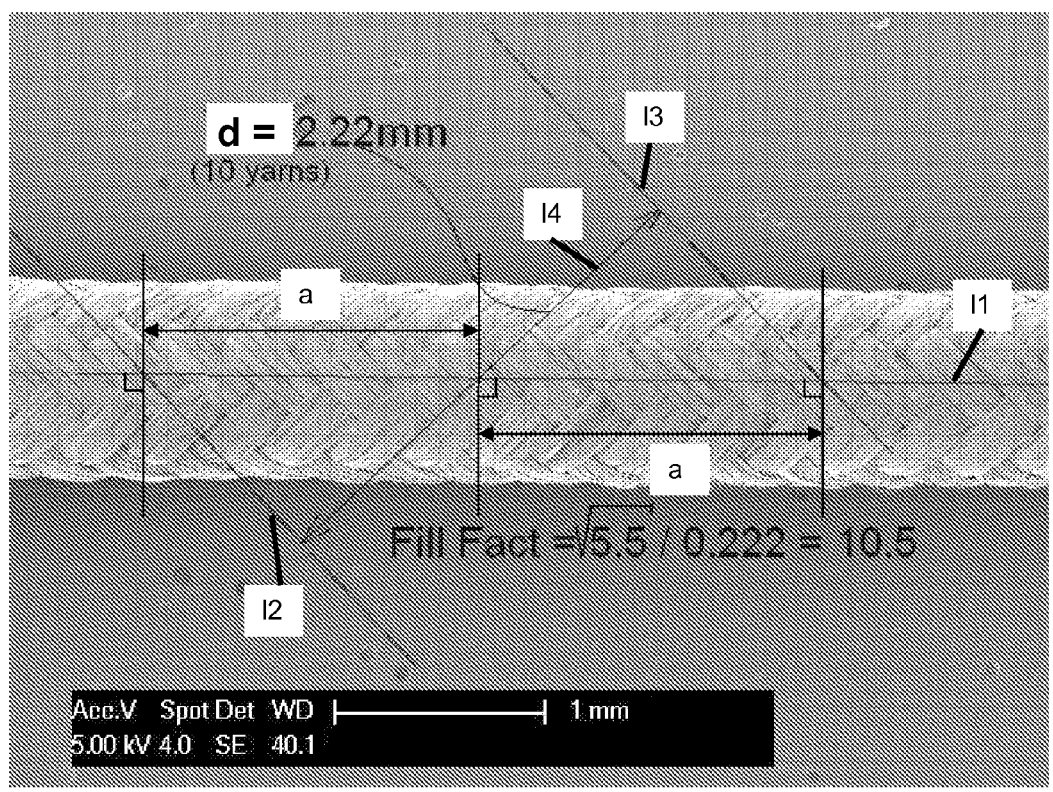
FIG. 4 shows details of calculation of the fill factor.
Figure 5:
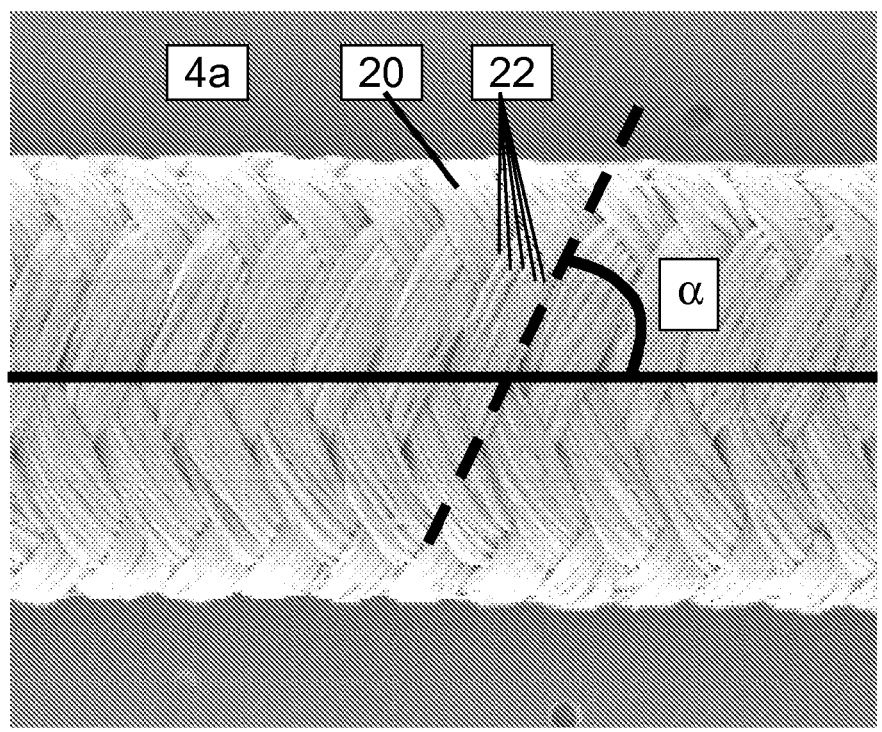
FIG. 5 shows the braiding angle the sheath.

In FIG. 4, the measurement and calculation is illustrated. The average distance between two parallel yarns, d, is measured by Scanning Electron Microscopy on a straight piece of yarn construction. Draw a (virtual) line, I1, arranged longitudinally over the center of the braid. Chose a first yarn and draw a (virtual) line, I2, parallel to the local yarn direction at the location where the first yarn intersects I1. Count 10 yarns from the first yarn and draw a (virtual) line, I3, parallel to the local yarn direction at the location where the $10^{th}$ yarn intersects I1.

Find the middle of I1 between the two intersections of I2 and I3 with I1. Construct the shortest line I4 between I2 and I3 through I1. d is the length of I4 divided by 10. In the ideal case I2 and I3 are parallel and I4 is perpendicular to I2 and I3 but small deviations are likely.

Flexural Yield Strength

The multifilament yarn constructions are tested according to the standard ASTM D 790-07. However, some slight modifications from the method described in the standard are required to take into account the conditions of the present case.

ASTM D 790-07 assumes a span to depth ratio of 16 as the normal case. Paragraph 7.5 of the standard discusses the possibility to use a larger span-to-depth ratio. A larger ratio is recommended for high strength composites. The present specimens are not high strength composites, but the preferred components are high strength yarns, such as HPPE yarn. So reasons for the recommendation of a larger span-to-depth ratio apply to the present specimen as well, and the next larger recommended span-to-depth ratio of 32 has been adopted for the present specimens.

The second difference is the shape of the cross section. ASTM D 790-07 is written for specimens with rectangular cross sections. The cross sections of the multifilament yarn constructions according the invention are substantially circular. The use of other cross sections than the rectangular cross section described in ASTM D 790-07 does not violate the physics of the bending test. However, the formulas that translate loads to material stress and stiffness must be adapted to other geometries. The formulas in ASTM D 790-07 are derived from elementary beam theory. Beam theory also offers such formulas for circular cross sections. The changes are:

In equation (3) of ASTM D 790-07 for the flexural strength $\rho_f = 3PL/2bd^2$ is replaced by: $\rho_f = 8PL/\pi d^3$ In equation (6) of ASTM D 790-07 for the modulus $E_b = L^3 m/4bd^3$ is replaced by: $E_b = 4L^3 m/3\pi d^4$ ASTM D 790-07 discusses the strain level at which the strength is determined. This can be at maximum load, but also at a certain strain level. It is stated in ASTM D 790-07 that results at strains larger than 5% are not valid anymore. Of course this value is somewhat arbitrary. Surprisingly it was found that the multifilament yarn constructions according to the invention often show a maximum load at strain values somewhat above 5%. They are hence in principle beyond the stated validity of the standard. Nevertheless the maximum flexural yield strength, $\sigma_{max}$, are additionally reported in addition to the flexural yield strength at 5% strain, $\sigma_{5\%}$, (which is within the stated validity of ASTM D 790-07) is also reported.

The stress strain curve of the multifilament yarn construction according to the invention is slightly different from other materials. Yet many similarities exist. The toe at the onset of the curve as discussed in ASTM D 790-07 is also present during tests on the multifilament yarn construction according to the invention. This toe is due to slack etc. as discussed in ASTM D 790-07 and therefore neglected, so the modulus is derived from the steepest part of the curve, as recommended in the standard. Indeed most tests show a reasonably straight area in the load displacement diagram, after surpassing the "toe region". This reasonably straight area the region with the steepest slope and indeed shows characteristics of a real modulus and thus it is reported as $E_{true}$ in complete agreement to the recommendation of the standard, as presented in section 12.9.1 of ASTM D 790-07. The multifilament yarn construction according to the invention show a transition to a second linear region around about 2%-3% strain. This second linear region allows the determination of a secondary modulus that is additionally reported as $E_{sec}$. This is a secant modulus as discussed in paragraph 12.9.2 of the standard. Summarizing, the obtained results are:

TABLE 1

Meaning of symbols

| Symbol | Property | Comment |
|---|---|---|
| $\sigma_{5\%}$ | Apparent stress according to the assumption of elastic beam theory at 5% strain | Compliant ASTM D 790-07 |
| $\sigma_{max}$ | Maximum stress (corresponds to ultimate strength) | At larger strain value than accepted by ASTM D 790-07, yet informative value |
| $E_{true}$ | Modulus | Compliant to ASTM D 790-07 |
| $E_{sec}$ | Secondary modulus | Compliant to ASTM D 790-07. Secant modulus |

It should be observed that $\sigma_{5\%}$ is conservative evaluation of the stiffness of the multifilament yarn construction, as the maximum stress $\sigma_{max}$ (also corresponding to the ultimate strength) is higher than $\sigma_{5\%}$.

Exhausted Flexural Yield Strength

Traditional stiff cables are steel monolines due to low cost and high specific stiffness. Steel monolines are typically prone to considerable cold work upon bending and will hence typically exhibit major change in properties upon repeated bending and often even brake after only a few bending cycles so multiple reshaping virtually not possible.

Surprisingly, it was found that segments according the present invention showed low reduction of flexural yield stress upon repeatedly bending (hereinafter referred to as exhausted flexural yield stress, $\sigma_{5\%,5}$). In a preferred embodiment of the present invention, the exhausted flexural yield stress, $\sigma_{5\%,5}$, of the segment is more than 50% of flexural yield stress, $\sigma_{5\%}$. More preferably, $\sigma_{5\%,5}$ is more than 55% $\sigma_{5\%}$, and most preferably $\sigma_{5\%,5}$ of the segment is more than 70% of $\sigma_{5\%}$. A high exhausted flexural yield stress is highly advantageous in that yarn constructions comprising the segments of this embodiment may be reshaped multiple times by the end user (such as a surgeon) without the end user experiencing major change of the bending behaviour.

An individual feature or combination of features from an embodiment of the invention described herein, as well as obvious variations thereof, are combinable with or exchangeable for features of the other embodiments described herein, unless the person skilled in the art would immediately realize that the resulting embodiment is not physically feasible.

EXAMPLES

Example 1

Preparation of Core Construction

For the experimental work, cores are prepared on a Herzog RU 2/16-80 braiding machine by braiding 16 core yarns of core filaments in a one-over-one diamond braid. The core yarns had varying material type, yarn titer, and filament titer. The prepared cores are presented in Table 2.

TABLE 2

| | Cores | | |
|---|---|---|---|
| Core | Core yarn | Stitch level | Core titer |
| A | 16*1*220 HPPE Dyneema Purity ® SGX | 8.0 st./cm | 3880 dTex |
| B | 16*1*440 HPPE Dyneema Purity ® SGX | 7.4 st./cm | 7880 dTex |
| C | 16*1*280 Polyester (PES) 280 dTex, f48, 57 T | 8.0 st./cm | 4680 dTex |

All cores showed very low flexural yield strength with $\sigma_{5\%}$ and $\sigma_{max}$ below 1 N/mm².

Example 2

Braiding of Sheath Construction onto Core Construction

For the experimental work, sheaths are prepared on a Herzog RU 2/16-80 braiding machine by braiding 16 sheath yarns of sheath filaments. The sheaths were braided directly onto the cores prepared in Example 1. The sheath yarns had varying material type, yarn titer, and filament titer. The prepared multifilament yarn constructions are presented in Table 3.

Example 3

Determination of Braiding Angle

Braiding angles of the sheath was determined according to the method described above. Values are presented in Table 3.

Example 4

Measurement of Fill Factor of Sheath Layer

Fill factors of the sheath was measured according to the method described above. Values are presented in Table 3.

TABLE 3

| | | Samples | | | | | | |
|---|---|---|---|---|---|---|---|---|
| | | | Sheath | | | | Total | |
| Sample | Core | Material | Stitch level [st/cm] | Titer [dtex] | Fill factor | Braiding angle | Titer [dtex] | Diameter [mm] |
| 1 | A | I | 37 | 570 | 7.6 | 52° | 4450 | 0.88 |
| 2 | A | I | 40 | 760 | | 54° | 4640 | 0.88 |
| 3 | A | I | 50 | 850 | | 60° | 4730 | 0.89 |
| 4 | A | I | 60 | 1100 | 10.7 | 65° | 4980 | 0.88 |
| 5 | A | II | 30 | 1420 | 10.5 | 48° | 5300 | 0.97 |
| 6 | A | II | 40 | 1680 | | 57° | 5560 | 0.98 |
| 7 | A | II | 50 | 1850 | | 62° | 5730 | 0.99 |
| 8 | A | II | 55 | 2130 | 14.94 | 65° | 6010 | 0.99 |
| 9 | A | III | 15 | 4570 | 7.8 | 36° | 8450 | 1.24 |
| 10 | A | III | 20 | 5070 | 12.5 | 44° | 8950 | 1.25 |
| 11 | A | III | 25 | 5900 | | 52° | 9780 | 1.30 |
| 12 | A | III | 30 | 6340 | | 57° | 10220 | 1.31 |
| 13 | B | II | 30 | 1330 | 7.8 | 29° | 9210 | 1.30 |
| 14 | B | II | 35 | 1830 | | 33.5° | 9710 | 1.30 |
| 15 | B | II | 40 | 2000 | 9.8 | 38° | 9880 | 1.30 |
| 16 | B | II | 50 | 2360 | 11.5 | 48° | 10240 | 1.32 |
| 17 | B | II | 55 | 2520 | | 52° | 10400 | 1.34 |
| 18 | B | I | 35 | 630 | | 33° | 8510 | 1.24 |
| 19 | B | I | 40 | 710 | | 38° | 8590 | 1.24 |
| 20 | B | I | 50 | 1100 | | 47° | 8980 | 1.25 |
| 21 | B | I | 60 | 1210 | | 57° | 9090 | 1.25 |
| 22 | C | IV | 15 | 5320 | 7.2 | 36° | 10000 | 1.25 |
| 23 | C | IV | 20 | 5920 | 9.8 | 45° | 10600 | 1.25 |

TABLE 3-continued

| | | | Sheath | | | | Total | |
|---|---|---|---|---|---|---|---|---|
| Sample | Core | Material | Stitch level [st/cm] | Titer [dtex] | Fill factor | Braiding angle | Titer [dtex] | Diameter [mm] |
| 24 | C | IV | 25 | 6660 | 12.0 | 51° | 11340 | 1.26 |
| 25 | C | IV | 30 | 7490 | 12.4 | 56° | 12170 | 1.28 |
| 26 | C | III | 15 | 4630 | 6.0 | 36° | 9310 | 1.26 |
| 27 | C | III | 20 | 5200 | 6.6 | 44° | 9880 | 1.26 |
| 28 | C | III | 25 | 6070 | 7.0 | 51° | 10750 | 1.28 |
| 29 | C | III | 30 | 6820 | 7.4 | 57° | 11500 | 1.30 |
| 30 | A | IV | 15 | 5220 | 5.5 | 37° | 9100 | 1.21 |
| 31 | A | IV | 20 | 5770 | 6.3 | 45° | 9650 | 1.24 |
| 32 | A | IV | 25 | 6380 | 7.0 | 51° | 10260 | 1.28 |
| 33 | A | IV | 30 | 7020 | 7.4 | 57° | 10900 | 1.32 |

Sheath
I: 16*1*25 HPPE Dyneema Purity ® TG grade
II: 16*1*55 HPPE Dyneema Purity ® SGX grade
III: 16*1*220 HPPE Dyneema Purity ® SGX grade
IV: 16*1*280 PES Example 5

Measurement of Flexural Yield Strength

Flexural yield strength was measured according to the method described above. Values are presented in Table 4.

TABLE 4

Mechanical testing results

| Sample | $\sigma_{5\%}$ | $\sigma_{max}$ | $E_{true}$ | $E_{sec}$ | Stiffness evaluation |
|---|---|---|---|---|---|
| 1 | 12.1 | 13.8 | 186.2 | 1413.7 | 1 |
| 2 | 13.9 | 15.6 | 265.9 | 1498.3 | 1 |
| 3 | 17.8 | 19.8 | 319.5 | 2105.7 | 2 |
| 4 | 24.2 | 27.3 | 501.4 | 2801.7 | 2 |
| 5 | 8.9 | 9.6 | 174.5 | 814.5 | 1 |
| 6 | 10.9 | 11.9 | 282.7 | 1094.6 | 1 |
| 7 | 12.6 | 13.7 | 280.3 | 1251.9 | 2 |
| 8 | 16.24 | 17.54 | 311.7 | 1862.7 | 2 |
| 9 | 3.6 | 3.7 | 52.1 | 327.0 | 0 |
| 10 | 4.8 | 5.0 | 65.0 | 527.6 | 1 |
| 11 | 5.5 | 5.5 | 71.1 | 548.8 | 1 |
| 12 | 6.0 | 6.1 | 75.5 | 636.4 | 1 |
| 13 | 5.5 | 5.6 | 99.7 | 413.7 | 1 |
| 14 | 6.7 | 6.8 | 104.4 | 524.1 | 1 |
| 15 | 6.9 | 7.1 | 114.0 | 528.5 | 1 |
| 16 | 7.6 | 7.8 | 135.8 | 613.3 | 2 |
| 17 | 7.8 | 8.4 | 144.6 | 634.9 | 2 |
| 18 | 4.6 | 4.7 | 102.4 | 246.0 | 1 |
| 19 | 6.4 | 6.5 | 125.24 | 410.4 | 2 |
| 20 | 9.0 | 9.2 | 148.3 | 706.0 | 2 |
| 21 | 11.1 | 11.2 | 207.6 | 944.6 | 2 |
| 22 | 1.8 | 1.9 | 26.9 | 192.8 | 0 |
| 23 | 2.5 | 2.6 | 36.7 | 180.2 | 0 |
| 24 | 3.3 | 3.4 | 49.8 | 256.7 | 1 |
| 25 | 3.4 | 3.5 | 56.7 | 351.4 | 1 |
| 26 | 2.3 | 2.5 | 42.5 | 174.1 | 0 |
| 27 | 3.3 | 3.5 | 56.6 | 240.6 | 0 |
| 28 | 4.9 | 4.9 | 97.2 | 360.5 | 0 |
| 29 | 4.8 | 4.9 | 82.3 | 375.7 | 0 |
| 30 | 1.8 | 1.9 | 101.6 | 33.1 | 0 |
| 31 | 2.6 | 2.7 | 169.7 | 52.7 | 0 |
| 32 | 3.0 | 3.1 | 216.3 | 57.9 | 1 |
| 33 | 4.2 | 4.4 | 359.8 | 86.8 | 1 |

The "Stiffness evaluation" is a qualitative evaluation where 2 indicates very high stiffness of multifilament yarn construction; 1 indicates stiff multifilament yarn construction; 0 indicates low but still measurable stiffness of multifilament yarn construction.

From the results in Table 4 it is observed that the stiffness as indicated by $\sigma_{5\%}$ and $\sigma_{max}$ of the multifilament yarn constructions according to the invention is a complex function of a number of parameters. However, a number of trends are observed. In general, it was found that the higher the braiding angle, the stiffer the multifilament yarn construction. Furthermore, the higher the fill factor, the stiffer the multifilament yarn construction. Finally, the highest stiffness was observed for samples having a lower area-% of sheath than core.

Example 6

Measurement of Exhausted Flexural Yield Strength

The sample consists of a 1 meter piece of the segment to be investigated. At the middle of the sample (50 cm from both ends) the segment is bend at an angle of 90° over an edge with a curvature having a radius of 1 mm, whereafter the segment is straightened. The bending is conducted 5 times at the same place whereafter the flexural yield stress (referred to as exhausted flexural yield stress, $\sigma_{5\%,5}$) is measured as described elsewhere at the same place. The exhausted flexural yield stress is compared to flexural yield stress of a sample not being exposed to the repeated bending.

The results are summarized in Table 5.

TABLE 5

Exhausted flexural yield stress

| Sample | $\sigma_{5\%}$ [N/mm²] | $\sigma_{5\%,5}$ [N/mm²] | $\sigma_{max}$ [N/mm²] | $\sigma_{max,5}$ [N/mm²] |
|---|---|---|---|---|
| 1 | 12.1 | 7.0 (=58% $\sigma_{5\%}$) | 13.8 | 7.6 (=55% $\sigma_{max}$) |
| 4 | 24.2 | 14.9 (=61% $\sigma_{5\%}$) | 27.3 | 16.0 (=58% $\sigma_{max}$) |

In Table 5 it is observed that the exhausted flexural yield stress of samples A and B according to the invention is more than 50% of the flexural yield stress of the of samples not being exposed to repeatedly bending.

Example 7

Compactness of Multifilament Yarn Construction

Three samples were prepared according to the specifications in Table 6.

TABLE 6

Specifications for samples 34, 35 and 36.

| No | Description | Titer | Diameter | Comments |
|---|---|---|---|---|
| 34 | Core:<br>16 × 1 × 220 SGX 8 st/cm<br>Sheath:<br>6 × 1 × 55 SGX 15 st/cm | 489 tex | 1.25 mm | Comparative sample.<br>Low flexural yield stress |
| 35 | Core:<br>16 × 1 × 220 SGX 8 st/cm<br>Sheath:<br>16 × 1 × 55 SGX 47 st/cm | 567 tex | 0.930 mm | High flexural yield stress |
| 36 | Core:<br>2 × 1760 SK75<br>Sheath:<br>16 × 1 × 25 62.0 st/cm | 462 tex | 0.800 mm | High flexural yield stress |

SGX: HPPE Dyneema Purity® SGX grade
SK75: HPPE Dyneema SK75 grade

Figure 6:
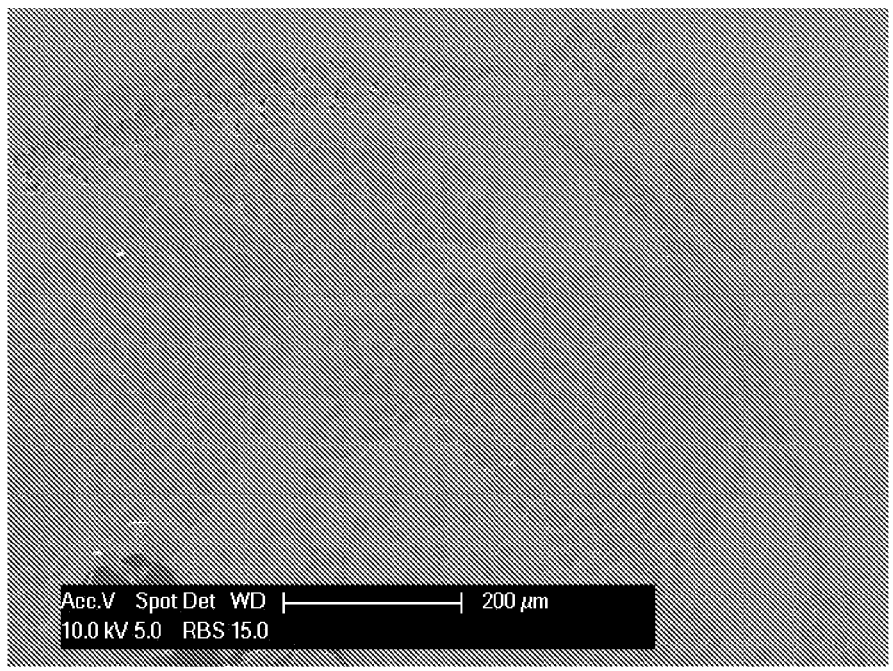
FIG. 6 shows details of a cross section of sample 34.
Figure 7:
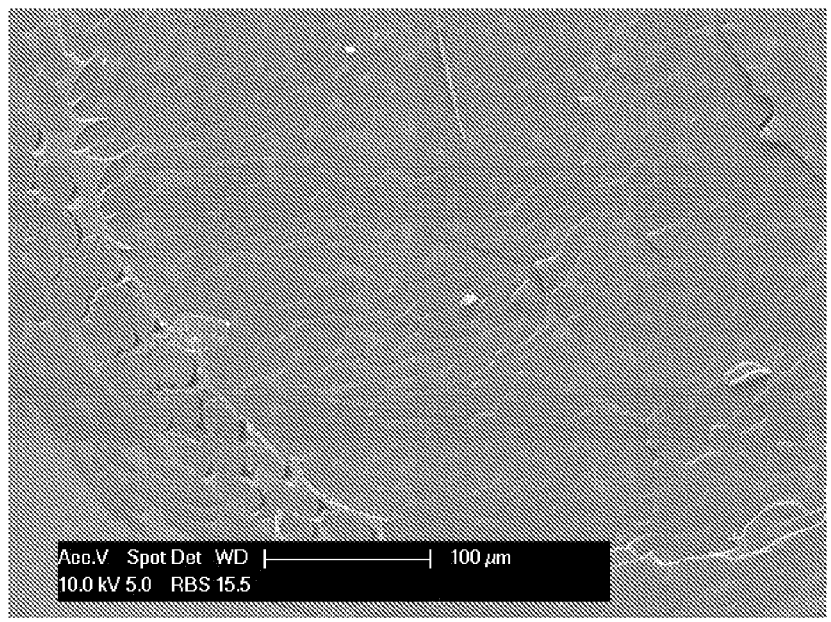
FIG. 7 shows details of a cross section of sample 35.

Scanning electron micrographs of sample 34 is shown in FIG. 6 and of sample 35 in FIG. 7. In FIG. 6, the filaments (dark spots) are arranged as discrete spots with large areas with the lighter resin used for preparation of the images. In FIG. 7, the filaments are very closely arranged and it is clearly observed that most of the filaments are heavily deformed. The sheath is still observed as a separate area, but the space between the core and the sheath is very little and only small amounts of the lighter resin phase is observed.

Theoretical cross section area is calculated based on the formula $D=0.0357\sqrt{T/\rho}$, where D is the theoretical diameter of the cross section, T is the Titer in tex of the multifilament yarn construction, and $\rho$ is the density of the multifilament yarn. The calculated cross sectional areas are presented in Table 7.

TABLE 7

Cross sectional areas

| No | Cross section area of construction, a, [mm²] | Theoretical cross section area of construction, A [mm²] | Ratio a/A | Comments |
|---|---|---|---|---|
| 34 | 1.45 | 0.64 | 2.45 | Large amounts of resin observed inside construction |
| 35 | 0.86 | 0.74 | 1.17 | Very limited resin observed inside construction |
| 36 | 0.64 | 0.60 | 1.06 | Virtually no resin observed inside construction |

From Table 7 it is observed that constructions with very low a/A ratio has been realized.

The invention claimed is:

1. A multifilament yarn construction comprising a core part and a sheath part, the core part comprising a plurality of core filaments, and the sheath part comprising a plurality of sheath filaments, wherein
   the sheath part is between 4 to 75 area-% of a cross section of the multifilament yarn construction,
   the sheath part is braided onto the core part,
   the braiding angle (α) of the sheath part is at least 30°,
   the width of the multifilament yarn construction is between 0.2 to 5 mm, and
   the flexural yield stress, $\sigma_{5\%}$, of the multifilament yarn construction is at least 3 N/mm².

2. The multifilament yarn construction according to claim 1, wherein a ratio (a/A) of a cross-sectional area of the multifilament yarn construction (a) to a theoretical cross-sectional area of the multifilament yarn construction (A) is at most 1.5.

3. The multifilament yarn construction according to claim 2, wherein the ratio a/A is at most 1.2.

4. The multifilament yarn construction according to claim 1, wherein the sheath part has a fill factor of at least 7.

5. The multifilament yarn construction according to claim 4, wherein the fill factor is at least 10.

6. The multifilament yarn construction according to claim 4, wherein the fill factor is below 20.

7. The multifilament yarn construction according to claim 1, wherein the construction has an exhausted flexural yield stress, $\sigma_{5\%,5}$ which is more than 45% of the flexural yield stress $\sigma_{5\%}$.

8. The multifilament yarn construction according to claim 1, wherein the core part is at least 30 area-% of a cross section of the multifilament yarn construction.

9. The multifilament yarn construction according to claim 8, wherein the core part is at least 80 area-% and at most 94 area-% of the cross section of the multifilament yarn construction.

10. The multifilament yarn construction according to claim 1, wherein at least 50 weight-% of the plurality of core filaments of the multifilament yarn construction and/or at least 50 weight-% of the sheath filaments of the multifilament yarn construction are synthetic fibers selected from the group consisting of polypropylene fibers, nylon fibers, polyester fibers, polyethylene fibers, aramid fibers and polyaramid fibers.

11. The multifilament yarn construction according to claim 10, wherein at least 90 weight-% of the plurality of core filaments and/or at least 90 weight-% of the sheath filaments of the multifilament yarn construction are the synthetic fibers.

12. The multifilament yarn construction according to claim 10, wherein at least 90 weight-% of the plurality of core filaments and/or at least 90 weight-% of the sheath filaments of the multifilament yarn construction are selected from the group consisting of high performance polyethylene fibers and high performance aramid fibers.

13. The multifilament yarn construction according to claim 1, wherein the braiding angle (α) of the sheath part of the multifilament yarn construction is at least 33°.

14. The multifilament yarn construction according to claim 13, wherein the braiding angle (α) is at least 35°.

15. The multifilament yarn construction according to claim 13, wherein the braiding angle (α) is at least 40°.

16. The multifilament yarn construction according to claim 1, wherein the braiding angle (α) of the sheath part of the multifilament yarn construction is at most 75°.

17. The multifilament yarn construction according to claim 1, wherein the core filaments of the multifilament yarn construction comprise at least 25 filaments.

18. The multifilament yarn construction according to claim 17, wherein the core filaments have an arrangement of either:
   (i) in parallel;
   (ii) in parallel with a twist of less than 100 turns per meter;
   (iii) with the filaments arranged in at least 3 multifilament yarns arranged in a braided, plaited, plied or twisted construction; or
   (iv) in a combination of at least two of the arrangements (i)-(iii).

19. The multifilament yarn construction according to claim 1, wherein the flexural yield stress, $\sigma_{5\%}$, of the multifilament yarn construction is at least 5 N/mm² and less than 50 N/mm².

20. A member comprising a multifilament yarn construction according to claim 1.

21. The member according to claim 20, wherein the member is a fishing line, a rope, a fishing net, a cargo net, an antiballistic article, a kite line or a medical product.

22. The member according to claim 20, wherein the member is a medical product selected from the group consisting of a medical implant, a medical repair product, a suture, a cable or a mesh.

23. The member according to claim 20, further comprising a further multifilament yarn construction which is different from the multifilament yarn construction.

24. The member according to claim 23, wherein the further multifilament yarn construction is arranged near an end of the member.

\* \* \* \* \*